United States Patent
Wang et al.

(10) Patent No.: US 7,365,201 B2
(45) Date of Patent: Apr. 29, 2008

(54) PROCESS FOR THE PREPARATION OF THE BORON DIFLUORIDE CHELATE OF QUINOLONE-3-CARBOXYLIC ACID

(75) Inventors: Zhi-Xian Wang, Brantford (CA); Murali Kondamreddy, Brantford (CA); Joseph DiMartino, Brantford (CA); Bhaskar Reddy Guntoori, Brantford (CA)

(73) Assignee: Apotex Pharmachem Inc., Brantford, ON ( * ) Notice: Subject to any disclaimer, the term of this patent is extended or adjusted under 35 U.S.C. 154(b) by 0 days.

(21) Appl. No.: 11/365,598

(22) Filed: Mar. 2, 2006

(65) Prior Publication Data

US 2007/0208174 A1    Sep. 6, 2007

(51) Int. Cl.
*C07F 5/02* (2006.01)
*C07D 491/08* (2006.01)

(52) U.S. Cl. ............................................ 546/13; 546/90
(58) Field of Classification Search .................. 546/13, 546/90

See application file for complete search history.

(56) References Cited

U.S. PATENT DOCUMENTS 4,940,794 A * 7/1990 Hermecz et al. .............. 546/13
4,980,470 A   12/1990 Masuzawa et al.

FOREIGN PATENT DOCUMENTS

WO   WO 2004/101527 A1   11/2004
WO   WO 2005/047260 A1   5/2005

* cited by examiner

*Primary Examiner*—Charanjit S. Aulakh
(74) *Attorney, Agent, or Firm*—Ivor M. Hughes; Neil Hughes; Francis Ng-Cheng-Hin

(57) ABSTRACT

A process for the preparation of the boron difluoride chelate of 1-cyclopropyl-6,7-difluoro-1,4-dihydro-8-methoxy-4-oxo-3-quinolone carboxylic acid via:

(a) the reaction of 1-cyclopropyl-6,7-difluoro-1,4-dihydro-8-methoxy-4-oxo-3-quinolone carboxylic acid ethyl ester with, (b) fluoroboric acid in the presence of poly(methylhydrosiloxane) or hexamethyldisiloxane.

2 Claims, No Drawings

PROCESS FOR THE PREPARATION OF THE BORON DIFLUORIDE CHELATE OF QUINOLONE-3-CARBOXYLIC ACID

FIELD OF THE INVENTION

The present invention relates to a process for the preparation of the boron difluoride chelate of quinolone-3-carboxylic acid of formula I,

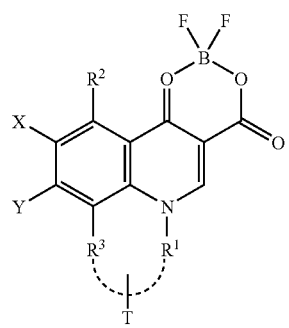

wherein $R^1$ is selected from the group consisting of a $C_{1-5}$ alkyl, a substituted $C_{1-5}$ alkyl, a $C_{3-6}$ cycloalkyl, a substituted $C_{3-6}$ cycloalkyl, and aryl; $R^2$ is selected from the group consisting of hydrogen, $C_{1-5}$ alkyl, $C_{1-5}$ alkoxy, amino, $C_{1-5}$ alkylamino, and $C_{1-5}$ acylamino group; $R^3$ is selected from the group consisting of hydrogen, halogen, $C_{1-5}$ alkoxy, amino, $C_{1-5}$ alkylamino, and $C_{1-5}$ acylamino group; or when $R^3$ is O or S forms an optionally substituted 5-, 6- or 7-membered ring T with $R^1$, or if the ring T is substituted, the substituent is $C_{1-5}$ alkyl, substituted $C_{1-5}$ alkyl, $C_{3-6}$ cycloalkyl, substituted $C_{3-6}$ cycloalkyl or aryl; X is hydrogen, chloride or fluoride; and Y is chloride or fluoride.

The boron difluoride chelate of quinolone-3-carboxylic acid of formula I can be further converted to quinolone antibacterial agents such as Norfloxacin, Ciprofloxacin, Ofloxacin, Levefloxacin, Gatifloxacin, Difloxacin, Perfloxacin and Enrofloxacin.

BACKGROUND OF THE INVENTION

The boron difluoride chelate of quinolone-3-carboxylic acid is an important intermediate for the preparation of quinolone antibacterial agents such as Norfloxacin, Ciprofloxacin, Ofloxacin, Levefloxacin, Gatifloxacin, Difloxacin, Perfloxacin and Enrofloxacin. The chelate I is usually prepared by the reaction of quinolone-3-carboxylic acid derivative II and fluoroboric acid ($HBF_4$) or trifluoroborane ($BF_3$):

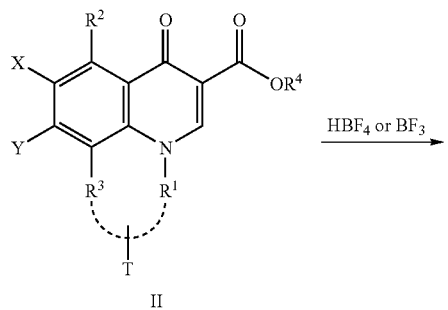

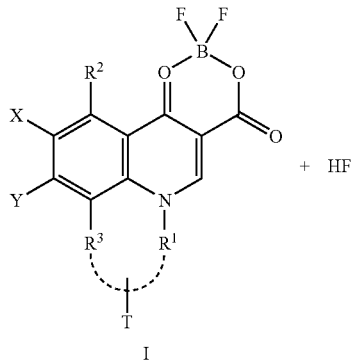

A byproduct of the reaction is hydrogen fluoride, a highly corrosive acid which can cause extremely painful and slow-healing burns and ulcers in humans. It etches glass and corrodes most substances except lead, polyethylene wax, and platinum (Encyclopedia of Reagents for Organic Synthesis, vol. 4, p. 2699, hereby incorporated as reference). These deficiencies dramatically limit the application of this reaction, especially for commercial scale production.

It was reported in the prior art that quinolone-3-carboxylic acid or its esters react with aqueous fluoroboric acid solution to form the chelate, for instance, those reported in WO 2004/101527 and U.S. Pat. No. 4,980,470. However, when these reactions are performed in glass-flasks or glass-lined reactors, the hydrogen fluoride formed reacts with the glass, generating insoluble inorganic fluoro-silicon compounds which are very difficult to remove from the product. The hydrogen fluoride byproduct also severely damages flasks or reactors and poses serious safety and operational problems. When these reactions are performed in non-glass equipment, such as stainless steel or Hastelloy® reactors, the reactions only produce quinolone-3-carboxylic acid (via ester hydrolysis or recovered starting material), and chelate formation is not observed.

It was also reported in WO 2005/047260 that the boron difluoride chelate of quinolone-3-carboxylic acid was formed from a quinolone-3-carboxylic acid silyl ester. However, in this process, quinolone-3-carboxylic acid has to be pre-converted into its silyl ester with a silylating agent such as hexamethyidisilazane or chlorotrimethylsilane.

It is therefore an object of this invention to provide a more industrially applicable process for the preparation of the boron difluoride chelate of quinolone-3-carboxylic acid which overcomes the deficiencies of the prior art processes.

It is a further object of the invention to provide silicon-containing compounds containing at least one silicon-oxygen bond which are useful in the formation of the boron difluoride chelate of quinolone-3-carboxylic acid.

It is a further object of the invention to provide a process for converting the boron difluoride chelate of quinolone-3-carboxylic acid into quinolone antibacterial agents.

Further and other objects of the invention will become apparent to those skilled in the art when considering the following summary of the invention and the more detailed description of the embodiments of the invention described herein.

SUMMARY AND DETAILED DESCRIPTION OF THE INVENTION

According to one aspect of the invention, a process is provided for the preparation of the boron difluoride chelate of quinolone-3-carboxylic acid of formula I,

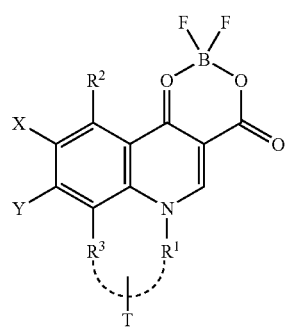

wherein $R^1$ is selected from the group consisting of a $C_{1-5}$ alkyl, a substituted $C_{1-5}$ alkyl, a $C_{3-6}$ cycloalkyl, a substituted $C_{3-6}$ cycloalkyl, and aryl; $R^2$ is selected from the group consisting of hydrogen, $C_{1-5}$ alkyl, $C_{1-5}$ alkoxy, amino, $C_{1-5}$ alkylamino, and $C_{1-5}$ acylamino group; $R^3$ is selected from the group consisting of hydrogen, halogen, $C_{1-5}$ alkoxy, amino, $C_{1-5}$ alkylamino, and $C_{1-5}$ acylamino group; or when $R^3$ is O or S forms an optionally substituted 5-, 6- or 7-membered ring T with $R^1$, or if the ring T is substituted, the substituent is $C_{1-5}$ alkyl, substituted $C_{1-5}$ alkyl, $C_{3-6}$ cycloalkyl, substituted $C_{3-6}$ cycloalkyl or aryl; X is hydrogen, chloride or fluoride; and Y is chloride or fluoride; via:
(a) the reaction of quinolone-3-carboxylic acid derivative II,

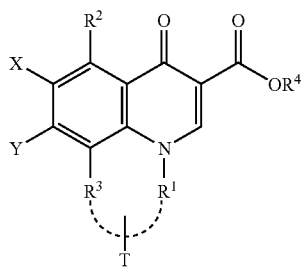

wherein $R^1$, $R^2$, $R^3$, T, X, and Y are as defined above and $R^4$ is hydrogen, $C_{1-5}$ alkyl, substituted $C_{1-5}$ alkyl, $C_{3-6}$ cycloalkyl, substituted $C_{3-6}$ cycloalkyl, alkylsilyl, aryl and arylalkyl; with:
(b) fluoroboric acid or trifluoroborane in the presence of a silicon-containing compound, wherein the silicon-containing compound contains at least one silicon-oxygen bond.

Surprisingly, we have discovered that the addition of a silicon-containing compound containing at least one silicon-oxygen bond can overcome the deficiencies in the prior art. First, the silicon-containing compound acts as a hydrogen fluoride scavenger and forms a stable fluoro-silica compound, which significantly reduces damage to the HF-susceptible production equipment and minimizes the safety hazards caused by the concomitantly produced hydrogen fluoride during unit operations. Secondly, we surprisingly discovered that the reaction of the silicon-containing compounds with hydrogen fluoride is a driving force for the formation of the chelate I, facilitating the reaction of quinolone-3-carboxylic acid and fluoroboric acid in non-glass equipment. Thirdly, the stable fluoro-silica compounds produced are typically volatile liquids or gases, which are readily removed and do not contaminate the chelate I and/or the final quinolone antibacterial agent product. Fourthly, the silicon-based products of this type are often of a low or non-toxic nature and have been used in household, personal care, and healthcare products, as well as industrially in automobiles, electronics, textiles, paper, construction, architecture, and in the food industry, and are widely available and inexpensive.

The silicon-containing compound is selected from the group consisting of silica gel, silica gel derivatives, silicon oxide, siloxanes and hydrosiloxanes. The preferred silicon-containing compounds are siloxanes and hydrosiloxanes. Siloxanes and hydrosiloxanes are a class of organic or inorganic chemical compounds of silicon, oxygen, and usually carbon and hydrogen, based on the structural unit $R_2SiO$, where R is an alkyl group or hydrogen. The more preferred siloxanes and hydrosiloxanes are selected from the group consisting of hexamethyldisiloxane (HMDSO), poly(dimethylsiloxane) (PDMS), poly(diethylsiloxane), poly(m-ethylhydrosiloxane) (PMHS), methyldimethoxy polydimesiloxane, octamethylcyclotetrasiloxane, hexamethylcyclohexasiloxane, and hexamethylcyclotrisiloxane.

The amount of the silicon-containing compound used in the reaction can be calculated based on the single silicon structural unit. The preferred amount of the silicon-containing compound is from about 1 to about 20 equivalent silicon units per unit of quinolone-3-carboxylic acid derivative II, and more preferably from about 2 to about 10 equivalent silicon units.

The reaction may be carried out neat or in the presence of a solvent. The preferred solvents are selected from the group consisting of water, ether, tetrahydrofuran and 1,4-dioxane. The reaction temperature is in the range from about 50° C. to about 150° C., preferably from about 90° C. to about 120° C.

According to another aspect of the invention, the boron difluoride chelate of quinolone-3-carboxylic acid I prepared according to the present invention can be further converted into quinolone antibacterial agents such as Norfloxacin, Ciprofloxacin, Ofloxacin, Levefloxacin, Gatifloxacin, Difloxacin, Perfloxacin and Enrofloxacin via N-arylation with an amine compound followed by chelate-hydrolysis.

The following non-limiting examples further illustrate the manner of carrying out the inventive process described herein.

EXAMPLE 1

A 1L Hastelloy® reactor was charged with 1-cyclopropyl-6,7-difluoro-1,4-dihydro-8-methoxy-4-oxo-3-quinolone carboxylic acid ethyl ester (50 g), 48% fluoroboric acid (200 mL) and hexamethyldisiloxane (50.6 g). The reactor was fitted with a condenser and the outlet of the condenser is connected to a trap containing sodium hydroxide. The mixture was stirred under nitrogen and heated to about 100° C. After stirring at this temperature for 7 hours, the mixture was cooled to room temperature and diluted with water (200 mL). The mixture was filtered and the filter-cake was washed with water. The solid was dried under vacuum to give boron difluoride chelate of 1-cyclopropyl-6,7-difluoro- 1,4-dihydro-8-methoxy-4-oxo-3-quinolone carboxylic acid as a light yellow crystalline solid (48.82 g, 92% yield).

EXAMPLE 2

A 1L Hastelloy® reactor was charged with 1-cyclopropyl-6,7-difluoro-1,4-dihydro-8-methoxy-4-oxo-3-quinolone carboxylic acid ethyl ester (50 g), 48% fluoroboric acid (200 mL) and poly(methylhydrosiloxane) (50 g). The reactor was fitted with a condenser and the outlet of the condenser was connected to a trap containing sodium hydroxide. The mixture was stirred under nitrogen and heated to about 100° C. After stirring at this temperature for 7 hours, the mixture was cooled to room temperature and diluted with water (200 mL). The mixture was filtered and the filter-cake was washed with water. The solid was dried under vacuum to give boron difluoride chelate of 1-cyclopropyl-6,7-difluoro-1,4-dihydro-8-methoxy-4-oxo-3-quinolone carboxylic acid as a light-yellow crystalline solid (50 g, 95% yield).

As many changes can be made to the invention without departing from the scope of the invention, it is intended that all material contained herein be interpreted as illustrative of the invention and not in a limiting sense.

The invention claimed is:

1. A process for the preparation of boron difluoride chelate of 1-cyclopropyl-6,7-difluoro-1,4-dihydro-8-methoxy-4-oxo-3-quinolone carboxylic acid comprising reacting 1-cyclopropyl-6,7-difluoro-1,4-dihydro-8-methoxy-4-oxo-3-quinolone carboxylic acid ethyl ester with fluoroboric acid in the presence of poly(methylhydrosiloxane).

2. A process for the preparation of boron difluoride chelate of 1-cyclopropyl-6,7-difluoro-1,4-dihydro-8-methoxy-4-oxo-3-quinolone carboxylic acid comprising reacting 1-cyclopropyl-6,7-difluoro-1,4-dihydro-8-methoxy-4-oxo-3-quinolone carboxylic acid ethyl ester with fluoroboric acid in the presence of hexamethyldisiloxane.

* * * * *